United States Patent [19]
Kriege

[11] 4,048,486
[45] Sept. 13, 1977

[54] LIGHTING DEVICE FOR FIBER-OPTIC SYSTEMS

[75] Inventor: Wolfgang Kriege, Mainz, Germany

[73] Assignee: Jenaer Glaswerk, Schott & Gen., Mainz, Germany

[21] Appl. No.: 630,623

[22] Filed: Nov. 10, 1975

[30] Foreign Application Priority Data
Nov. 22, 1974 Germany .............................. 2455333

[51] Int. Cl.² .......................... G02B 5/16; F21S 1/14
[52] U.S. Cl. .................................. 240/1 R; 350/96 B; 355/1
[58] Field of Search ................. 240/1 R, 1 LP, 10 L, 240/41.35 A, 81, 41.35 B; 355/70, 1; 350/96 B, 96 BC

[56] References Cited
U.S. PATENT DOCUMENTS

| | | | |
|---|---|---|---|
| 3,825,335 | 7/1974 | Reynolds | 240/1 LP |
| 3,887,279 | 6/1975 | Rubin | 355/70 X |
| 3,897,147 | 7/1975 | Simon | 355/70 X |

OTHER PUBLICATIONS

IBM Technical Disclosure, "Fiber Optic Connectors," R. J. Lynch, vol. 13, No. 2, July 1970, p. 533.

*Primary Examiner*—Edna M. O'Connor
*Attorney, Agent, or Firm*—Littlepage, Quaintance, Murphy, Richardson & Webner

[57] ABSTRACT

The invention consists of a device for lighting the light entering ends of a light guide consisting of at least two light guiding fibers, said lighting done by means of two light sources, by which, either singly or using both sources together, the receiving-ends of the light guides are illuminated.

10 Claims, 4 Drawing Figures

LIGHTING DEVICE FOR FIBER-OPTIC SYSTEMS

BACKGROUND

The application of fiber-optic light guides and lighting systems has proved itself, for example, in the area of medicine, in signaling means or in optical electronics and new possibilities have been created.

Through the advantageous use of light guides in different optical systems, large numbers of light sources are often replaced by a single light source, but this places a high requirement on such a single light being trouble-free. Thus, for a fiber optic system to work dependably where the lighting of such a system is done by a single source, the aging of the single light source often presents an untolerable uncertainty factor.

The problem of the reliability of the single light source has not been satisfactorily solved. In medical areas there are known systems in which when a lamp fails, a new lamp can be raised through a mechanical pivot by mechanical displacement of the light guides to a new lamp.

In the area of signaling devices a help in overcoming this problem is known in which one can operate with a duplicate fiber-optic system.

Even in conventional optics was it possible only with considerable technical expenditure to lead the emitted light from different light sources selectively or jointly to the same beam-entrance for lighting of an optical system. Yet even with consideration of this kind of solution no identical lighting division could be devised for a single light source.

An arrangement for beam dividing is, of course, known in which the light from a light source can be divided in two by means of partially light-transmitting mirror, placed at an angle to the beam of light.

By the appropriate arrangement of a partially light-transmitting mirror, the beam from a lamp can be divided into two equal beam segments. With such a beam divider it is possible to postulate a second light source arranged such that the beam from it can be divided into two equal segment beams which can be superimposed with the segment beams of the first light source.

In conventional optics, however, two such divided beam segments from light emitted in two different directions were unusable for lighting of a single optical system, because the problem of joint conductance of the beam remains just the same as it is in the employment of two individual light sources.

Only through the use of beam-splitting for lighting of a fiber optic system, however, is the problem of the reliability of the light source solved in a simple way.

It is to be sure known, that common light entrance ends of a fiber-optic light guide can be bifurcated into two strands in order, for example, to place different color filters in front of the strands to make possible the construction of multi-colored signals. This was however only done in order to be able to change the lighting from a single light source.

An application, in which, through a beam splitter, the light from a source is divided into two beam segments and beamed into two non-parallel entrance strands of a light guide and then is again changed into a common beam by reunification of these bifurcated strands, is unknown to the prior art apparently because of the senseless expense. Thus, the advantages that such an application offers in the possiblity of guiding the light from two light sources either singly or together into the same beam entrance has been overlooked.

The development of this illumination scheme is an object of the present invention; the aim of which is a lighting device using a fiber-optic system which is not dependent on a single light source and which leads the light of a second light source into the same beam-entrance which is lighted by a first light source.

SUMMARY OF THE INVENTION

This object is achieved according to the present invention by a lighting system which possesses two light sources with broadly directed beams, the optical axes of the beams of both light sources crossing each other at a point. In the area of this cross-point and in the direction of the angle bisector between these optical axes, a beam divider-mirror active on both sides is arranged through which the impinging beam from each light source is divided into two beam segments. The beam segments are generally congruent so that with each light source alone as well as with both light sources together the two entrances of a fiber-optic system which lies along the length of the optical axes of the light sources can be lighted at the same time.

Double-sided beam dividers of widely different design are well known. They differ in the relative amount and wave length of the light reflected and transmitted. These properties can additionally be dependent on the incident angle of the impinging light. Possibilities for differently derived lighting effects are obtained by using different beam splitters in the lighting device of the present invention.

In most cases, however, it is desired to light both entrances of a fiber-optic system selectively using, at times, both light sources to achieve equal intensity. In this case a beam splitter is used which reflects and transmits the same amount of impinging light at a specific angle with no color displacement. Such beam dividers are typically arranged at an angle of 45° to the path of the beam, however, endless variations are possible as long as the light from both sides enters at the same angle and the resulting arrangement remains symmetrical.

In one of the possible arrangements within the scope of the present invention, if in the normal course of operation of a light source a failure occurs, an automatic control added to the device can be arranged to switch on the other light source automatically. Thus, in the event of the failure of one light source, operation is immediately switched to the other light source. This, except for the short switching break, lessens the breaks in operations and the entrances of the fiber-optic system are again lighted with the same intensity, provided that both light sources have the same output rating. An optical or acoustical trouble-signal can indicate when it is necessary to change a defective lamp.

In addition to these uses which almost completely minimize the chances of lamp failure, the lighting device of the present invention has still other possibilities.

With a suitable control, which, for example, can be an automatic control for birghtness, one can provide a selective, common switch on the light sources which will make a stepwise adjustment of the light intensity to the surrounding brightness. This can be especially desirable in fiber-optics signal indicators. Thus, three linearly partitioned birghtness control steps can be obtained if the output ratings of the light sources are in the ratio of 1:2.

Moreover, such a stepwise arrangement to a lighting device according to the present invention can completely safeguard against lighting failure if, in the failure of a light source, the switching control is automatically bridged in a way such that the second light source is switched on and remains in operation.

The device according to the present invention is for lighting the entrance end of a light guide, which consists of at least two individual fibers, of the kind described. The fibers can be part of a fiber-optic light guide bifurcated at its entrance end into two equal fibers which can be lighted by light from one or both of the light sources. If one uses two light sources the same intensity and symmetrical beam splitting then for both fibers or strands of the light guide, whether lighted by one or the other light source, on finds that the same lighting strength comes to the individual light-guide fiber as comes when the fiber is lighted directly by the undivided light beam of one of the light sources.

This is then the proposition: if one uses a many-veined light guide, the quantity of light transported in the individual fibers is generally the same. In satisfying this hypothesis for light of one color it is unimportant as to which light-guide fiber of the many-veined guide leads to which of the two strands at the entrance end. Should, for example, however, light of different colors be irradiated into a strand of many-veined light guides, (which it is possible to achieve by using a color filter) then both strands, must, understandably, encompass those fibers which will give light of the same color at their ends.

It is possible to have two separated light guides which lead equal quantities of light to different places and are lighted by a single light-source, which in a known system leads to many-veined light-guides which guides can be further divided into strands and are directed to desired places. Thus, for application of the lighting device according to the invention as described above the light guide must be divided at its entrance end, and in this special case a junction of both strands is unnecessary. They can be led directly to where they are to be inserted. Even in this case, the advantages of the invention are maintained in that in the failure of one existing light source both light guides can be lighted with the same intensity by connecting the other light source in the same way.

The lighting device can be better understood by examining the FIGS. 1 to 4 and their description as follows:

DESCRIPTION OF THE PREFERRED EMBODIMENTS

Figure 1:
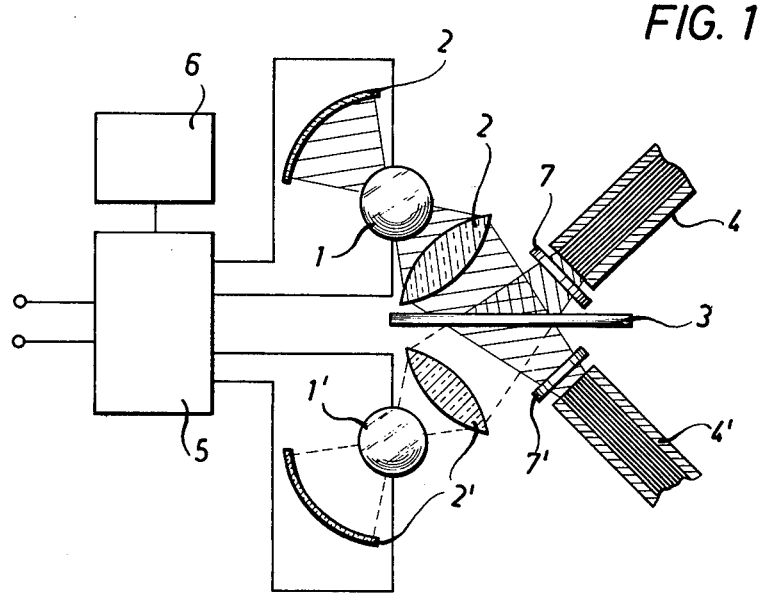
FIG. 1 is a schematic plan view partially in cross-section of a lighting device according to the invention.

The schematic construction in FIG. 1 shows an upper light source 8 consisting of a lamp 1 and a focus means 2 consisting of a concave mirror 15 and condenser lens 16. Correspondingly there is a lower light source 8' with lamp 1' and focus means 2'. The optical axes 17 and 17' of both light sources make a 90° angle with each other. At 45° to the optical axes 17, 17' of the light sources 8, 8' is a beam-splitting mirror 3 which is so arranged that the crossing point 18 of the optical axes lies in the plane of the beam-splitter 3. Along the length of the optical axes 17, 17' of the light sources 8, 8' beyond the beam splitter 3 is found the entrance ends 4 and 4' of one or two multi-veined light guides 19 and 19' respectively. These entrance ends 4, 4' can be connected for selective application to color filters 7 and 7'. The constructions designated 5 and 6 show automatic controls for lamps 1 and 1' which can be, for example, a brightness regulator or switching control as previously discussed. The hatching marks for the light beam as shown for lamp 1 indicates that this lamp is in operation while the dotted line around the beam means that lamp 1' is not in operation.

From the focus means 2 the beam from lamp 1 goes through the beam splitter 3 where it is divided into two segments, one which passes through the beam splitter 3 and continues in generally the same direction and enters into the light guide 4 and the other beam segment is reflected and enters into light guide 4'. In using lamp 1' the beam is similarly divided into two corresponding beam segments. It is not possible to know from observing the beam segments from which lamp the light is coming. By using both lamps together the beam segments can be made to overlap so that each of the light-guide entrances 4 and 4' receives practically the same amount of light as with using one lamp with the beam splitter 3 removed. The only decrease is caused by the absorption loss occurring at the beam-splitter 3.

Figure 2:
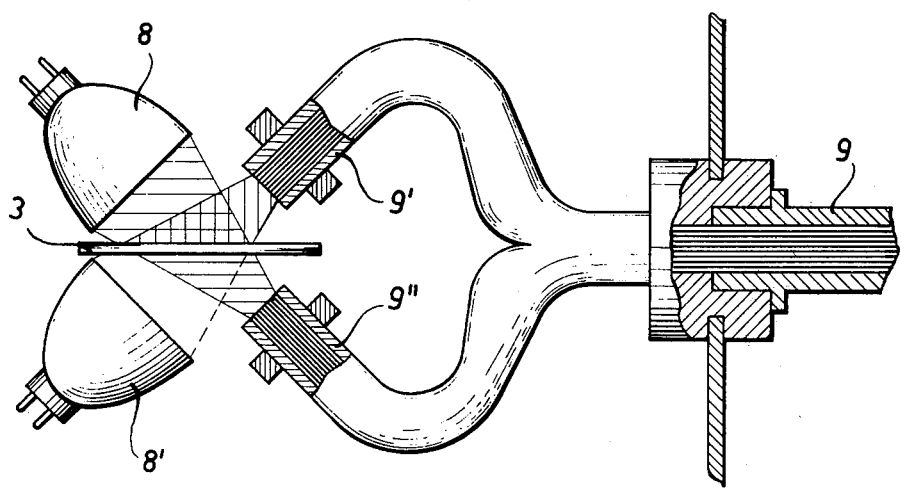
FIG. 2 is a schematic plan view partially in cross-section of a lighting device according to the invention for lighting one light entrance end of a many-veined light guide which guide has been bifurcated into two strands to receive light from a divided beam.

In the arrangement according to FIG. 2, two light sources 8 and 8' are shown, which are drawn to indicate that an elliposidal mirror 20, 20' serves for focusing the light. The beam segments generated through the beam splitter 3 enter into the entrance ends 9' and 9" which in turn are divisions from a multi-veined bifurcated light guide 9.

Each single fiber according to the arrangement of the invention transports the same amount of light, independent of whether the fiber empties into entrance ends 9' or 9" and independent of whether the light source 8 or 8' is in operation. Thereby the joined light guide 9 carries the full illumination of whatever lamp is switched on to wherever it is desired.

Figure 3:
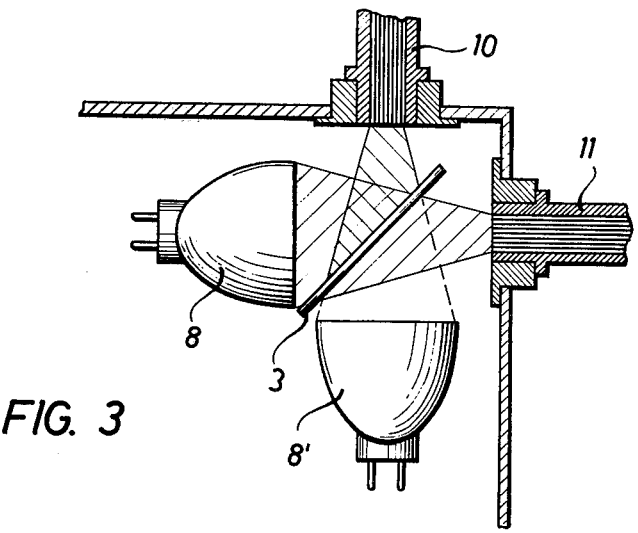
FIG. 3 is a schematic plan view partially in cross-section of a lighting device according to the invention for lighting two light guides with equal intensity.

FIG. 3 shows an arrangement, which differs from FIG. 2 only in that the lighting device according to the invention consists of the light sources 8 and 8' arranged so that beam segments from the beam splitter 3 light two separated light guides 10 and 11 and these light guides are not led or joined together. The ends of these separate light guides are intended for illumination at two different places. Such devices find application, for example, in medical use.

Figure 4:
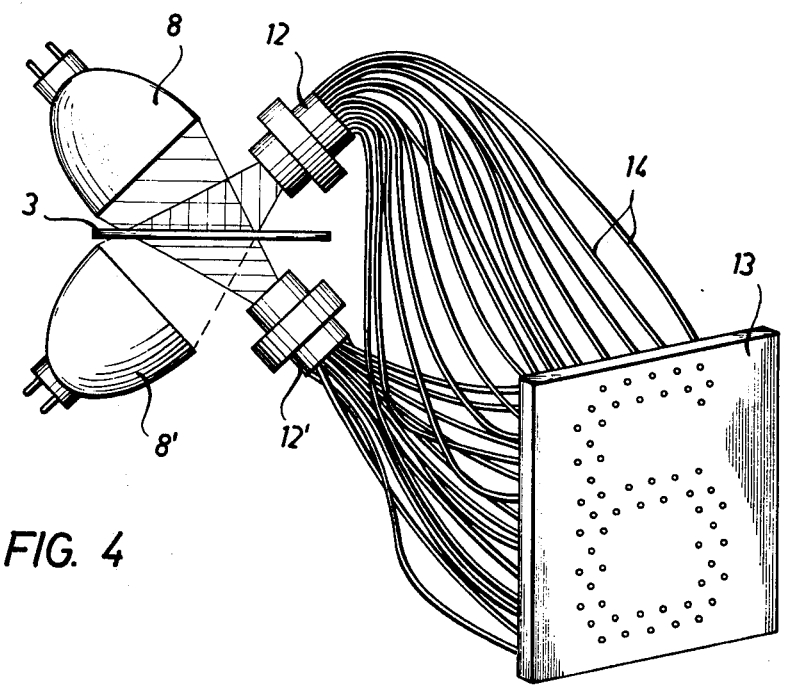
FIG. 4 is a perspective schematic view of a lighting device according to the invention for lighting of a fiber-optic digital-signal indicator by means of a many-veined light-guide.

In FIG. 4 is shown the application of the device according to the invention in the area of indicators. A multi-armed light guide 22 is at its end divided into a large number of individual strands 14, and each strand leads to a grating hole 21 of a signal board 13. The entrance end of the light guide 22 is joined together to two strands 12 and 12' which are lighted according to the invention. In this example it is especially clearly affirmed that in spite of the divided entrance, all fibers 14 transport the same amount of light, for the individual grating holes 21 of the lighted numbers show the same brightness. While the graphic drawing shows the individual arms 12 and 12' of the light guide 22 somewhat spread apart, it basically applies to any multi-armed light-guide, the light from which might be extinguished at times by a light source failure. A lighting device according to the present invention as illustrated in FIG. 4 would avoid the reproduction of maimed or curtailed figures or numbers due to the failure of a single light source.

Connecting color filters into the system makes the reproduction of multi-colored designs possible.

Further possible applications suggest themselves for the areas of light-bodies for punch cards and light barriers in which the light-transmitter utilizes fiber-optic elements. Here, as in all cases in which light is transmitted through fiber optic systems, a very high degree of reliability is necessary.

Although the invention has been described in considerable detail with reference to certain preferred embodiments thereof, it will be understood that variations and modifications can be effected within the spirit and scope of the invention as described above and as defined in the appended claims.

What is claimed is:

1. A device for illuminating a fiber-optical system comprising
   a. two light sources having broadly directed beams, each beam having an optical axis, the light sources arranged with respect to each other such that the optical axes of the beams intersect at a cross point,
   b. two light entrances to a fiber-optical system aligned with the optical axes of the light sources each located on the opposite side of the cross point from one of the sources, and
   c. a beam splitting mirror arranged in the region of the cross point for dividing the impinging light beam from each of the light sources into two segments such that two of said segments, one from each of the two light sources, are coincident upon one of said two light entrances.

2. An illuminating device according to claim 1 wherein the beam splitting mirror transmits and reflects from both sides approximately the same amount of the impinging light independent of the wave length of the light and through said beam splitting mirror the impinging light beam from each of both light sources is divided into two beam segments of equal intensity and color.

3. An illuminating device according to claim 1 wherein the optical axes of the impinging light beams of both light sources and the optical axes of the beam segments of each light source make an angle of 90° with each other.

4. An illuminating device according to claim 1 wherein said two entrances of a fiber optic system are the ends of two equal strands of a many-veined light guide.

5. An illuminating device according to claim 1 wherein both light sources are of equal intensity.

6. An illuminating device according to claim 1 wherein both light sources are of different intensities.

7. An illuminating device according to claim 6 wherein the intensities of the light sources are in the ratio of 1:2.

8. An illuminating device according to claim 1 further comprising color filters arranged in front of the entrances of the fiber-optics systems.

9. An illuminating device according to claim 1 wherein said beam splitting mirror divides the impinging beam of each of two light sources into two beam segments according to intensity and color.

10. An illuminating device according to claim 1 wherein said beam splitting mirror divides the impinging beam of each of two light sources into two beam segments according to intensity or color.

* * * * *